United States Patent [19]
// Raikhel

[11] Patent Number: 5,276,269
[45] Date of Patent: Jan. 4, 1994

[54] LECTIN CNDA AND TRANSGENIC PLANTS DERIVED THEREFROM

[75] Inventor: Natasha V. Raikhel, Okemos, Mich.

[73] Assignee: Board of Trustees operating Michigan State University, East Lansing, Mich.

[21] Appl. No.: 917,665

[22] Filed: Jul. 20, 1992

Related U.S. Application Data

[63] Continuation of Ser. No. 406,318, Sep. 12, 1989, abandoned.

[51] Int. Cl.⁵ .................. A01H 4/00; C12N 15/00
[52] U.S. Cl. ..................... 800/205; 800/DIG. 3; 435/172.1; 435/172.3; 435/240.4; 536/23.1; 536/23.6; 935/35; 935/67
[58] Field of Search .............. 800/205, 800/DIG 43; 435/240.4, 240.49, 172.3, 172.1, 69.1, 320.1; 536/23.1, 23.6; 935/67, 35

[56] References Cited

FOREIGN PATENT DOCUMENTS 0193259 9/1986 European Pat. Off. ...... C12N 15/00

OTHER PUBLICATIONS

Vaecd et al. (1987) XI Brazilian Congress of Entomology: pp. 427–435.
Osborn et al. (1988) Science vol. 240, pp. 207–210.
Barton et al. (1987) Plant Physiology vol. 85, pp. 1103–1109.
Murdock et al. (1990) Phytochemistry vol. 29 #1 pp. 85–89.
Murdick et al., Phytochemistry 1989.
Etzler, M. E. Plant lectins: molecular and biological aspects. Ann Rev Plant Physiol 36:209–234 (1985).
Stinissen, H. M. et al., Occurrence and immunological relationships lectins in gramineous species. Planta 159:105–111 (1983).
Mishkind, M. L., etc., Science 220:1290–1292 (1983).
Stinissen, H. M., et al., Planta 164:278–286 (1985).
Peumans, W. J., et al., Planta 154:562–567 (1982).
Smith, J. J. et al., Plant Physiol 89S:102 (1989).
Mishkind, M. L. et al, J. Cell Biol. 92:753–764 (1982).
Finkelstein, R. R., et al, Plant Physiol. 81:907–912 (1986).
Silflow, C. D., et al., Biochem 18:2725–2731 (1979).
Raikhel, N. R. et al., Proc. Natl. Acad. Sci. USA 84:6745–6749 (1987).
Feinberg, A. P. et al., Anal. Biochem. 132:6–13 (1983).
Mansfield, M. A. et al., Planta 173:482–489 (1988).
Gubler, U., et al., Gene 25:263–269 (1983).
Wilkins, T. A. et al., Plant Cell (in press).
Raikhel, N. V., et al., Planta 176:406–414 (1988).
Vieira, J., et al., Methods in Enzymology, vol. 153: 3–11 (1987).
Sanger, F., et al., Proc. Natl. Acad. Sci USA 74:5463–5467 (1977).
Mizusawa, S., et al., Nucl Acids Res. 14:1319–1324 (1986).
Dale, R. M. K., et al., Methods in Enzymology, 155:204–214 (1987).
Hondred D., et al., Plant Mol. Biol. 9:259–275 (1987).
Raikhel, N. V., et al., Planta. 162:55–61 (1984).
Triplett, B. A., et al., Dev. Biol. 91:491–496 (1984).
Towbin, H., et al., Proc Natl. Acad. Sci. USA 76:4350–4354 (1979).
Smith, J. J., et al., Plant Physiol. (submitted) (1989).
Riakhel, N. V., et al., In situ RNA hybridization in plant tissues Plant Molecular Biology Manual, Sect B9. Kluwer Acad. Publ., Dordr The Netherlands, pp. 1–32 (1988).
von Heijne G., Nucl. Acids Res. 14:4683–4690 (1986).
Peumens, W. J. et al., Biochem. J. 203:239–243 (1982).
Shinshi, H., et al., Proc. Natl. Acad Sci. USA 85:5541–5545 (1988).

(List continued on next page.)

Primary Examiner—Gary Benzion
Attorney, Agent, or Firm—Ian C. McLeod

[57] ABSTRACT

Transgenic plants containing cDNA encoding Gramineae lectin are described. The plants preferably contain cDNA coding for barley lectin and store the lectin in the leaves. The transgenic plants, particularly the leaves exhibit insecticidal and fungicidal properties.

11 Claims, 11 Drawing Sheets

OTHER PUBLICATIONS

Smith, J. J. et al., Plant Physiol. 89S:102 (1989).
Raikhel, N. V., et al., In TC Bog-Hansen, E van Driessche, eds., Lectins, vol. V, Walter de Gruyter & Co., Berlin pp. 75-81 (1986).
Lerner and Riakhel, Plant Physiol. 90 (in press) (1989).
Struhl, K., Biotechniques 3, 452-453 (1985).
Kunkel, T. A., et al., Methods Enzymol. 154:367-382 (1987).
An, et al., Plant Molec. Biol. Manual A3, 1-19 (1988).
Hooykaas, P. J. J., Plant Molec. Biol Manual A4, 1-13 (1988).
Horsch, R. B., et al., Plant Molec. Biol. Manual A5, 1-9 (1988).
Dellaporta, S. L., et al., Plant Molec. Biol. Rep. 1:19-21 (1983).
Wilkens and Raikhel, The Plant Cell 1:541-549 (1989).
Blake, et al., Anal. Biochem, 136:175-179 (1984).
Trimble, et al., Anal. Biochem. 141:515-522 (1984).
Guy, et al., Plant Physiol. 64:61-64 (1979).
Boller, et al., Plant Physiol. 63:1123-1132 (1979).
Shimomura, S., et al., Planta 175:558-566 (1988).

FIGURE 1

```
         M  K  M  S  I  R  A  L  A  L  G  A  A  A  V  L  A  F  A    -7
  1  CAGAAAACAAGAAGGATGAAGATGAGCACCAGGGCCCTCGCTCTCGGCGCCGGCGTCCTCGCCTTCGCG

A  A  I  A  H  A  Q  R  C  G  E  Q  G  S  N  M  E  C  P  N  N  L  C  C  S   19
 76  GCGGCGACCGCGCACGCCCAGAGGTGCGGCGAGCAGGGCAGCAACATGGAGTGCCCAACAACCTCTGCTGCAGC

Q  Y  G  Y  C  G  M  G  G  D  Y  C  G  K  G  C  Q  N  G  A  C  Y  T  S  K   44
151  CAGTACGGGTACTGCGGCATGGGCGGGGACTACTGCGGCAAGGGCTGCCAGAACGGCGCCTGCTACACCAGCAAG

R  C  G  T  Q  A  G  G  K  T  C  P  N  N  H  C  C  S  Q  W  G  Y  C  G  F   69
226  CGCTGCGGCACTCAGGCCGGCGGCAAGACATGCCCTAACAACCACTGCTGCAGCCAGTGGGGTTACTGCGGCTTC

G  A  E  Y  C  G  A  G  C  Q  G  P  C  R  A  D  I  K  C  G  S  Q  A  G      94
301  GGCGCCGAGTACTGCGGCGCCGGCTGCCAGGGCCCCTGCCGCGCCGACATCAAGTGCGGCAGCCAGGCCGGC

G  K  L  C  P  N  N  L  C  C  S  Q  W  Y  C  G  L  G  S  E  F  C  G  E      119
376  GGCAAGCTTTGCCCCAACAACCTCTGCTGCAGCCAGTGGTACTGCGGGCTCGGCTCCGAGTTCTGCGGGGAG

G  C  Q  G  G  A  C  S  T  D  K  P  C  G  K  A  A  G  G  K  V  C  T  N  N   144
451  GGCTGCCAGGGCGGTGCTTGCAGCACCGACAAGCCGTGCGGCAAGGCCGCCGGCGGCAAAGTTTGCACCAACAAC

Y  C  C  S  K  W  G  S  C  G  I  G  P  G  Y  C  G  A  G  C  Q  S  G  G  C   169
526  TACTGCTGCAGCAAGTGGGGATCCTGTGGCATCGGGCCCGGCTACTGCGGCGCAGGTTGCCAGAGCGGCGGCTGC

D  G  V  F  A  E  A  I  A  A  N  S  I  L  V  A  E  *  *
601  GACGGTGTCTTCGCCGAGGCCATCGCCGCCAACTCCATCTTGTCGCAGAATGATCTTGCTAATGGCAGTAT

676  TATTGCAACGACGAATAATCCGTGGCAGTTTTGTTGCCACGTACGGTCTCCCTTCACTTACTTTTAGCACTAGTC

751  CTTAATAATTCTCCAGCCTTGCAATATGACGTGCTACATGGACATGCAGTGAGAAGTACTG

826  TGTGGCAATATAGGGTGTACTATTGTTGCCACAAATTTAGTTCTTTTCTTGTTACGTACGTACAGTTGTCAGGATG

901  CATGCATCCCCGTTGTAATGTTGGAGTACTCCATGATTTCGTTGCAATATATATATTGCCATGAGTCTAAAG
```

1  2

21 kD -

1    2    3    4    5

23 kD -
18 kD -

```
                                          M   K   M   M   S   T
 1              ACCAGCACCAAGAAAACAAAAAGCATGAAGATGATGAGCACC    WGA-A
                                      M   R
 1                        AATAATGAGAAAGATGATGAGCACC           WGA-D

1                  CAGAAAACAAGAAGGATGAAGATGATGAGCACC         BARLEY

R   A   L   A   L   G   A   A   A   V   L   A   F   A   A   A   T   A   Q   A
 43  AGGGCCCTCGCGCTCGGCGCGGCTGCCGTCCTCGCCTTCGCCGCGGCGACCGCTCAGGCC    WGA-A
       M   T                   V   F
 26  ATGGCCCTTACGCTCGGCGCGGCTGTCTTCCTCGCCTTCGCCGCGGCGACCGCGCAGGCC    WGA-D
                                                                H
 34  AGGGCCCTCGCTCTCGGCGCGGCCGCCGTCCTCGCCTTCGCGGCGGCGACCGCGCACGCC    BARLEY
        *    **  *            * * *              *           *  *

Q   R   C   G   E   Q   G   S   N   M   E   C   P   N   N   L   C   C   S   Q
 103 CAGAGGTGCGGCGAGCAAGGCAGCAACATGGAGTGCCCCAACAACCTCTGCTGCAGCCAG    WGA-A

86  CAGAGGTGCGGCGAGCAGGGCAGCAACATGGAGTGCCCCAACAACCTCTGCTGCAGCCAG    WGA-D

94  CAGAGGTGCGGCGAGCAGGGCAGCAACATGGAGTGCCCCAACAACCTCTGCTGCAGCCAG    BARLEY
                     *

Y   G   Y   C   G   M   G   G   D   Y   C   G   K   G   C   Q   N   G   A   C
 163 TACGGGTACTGCGGGATGGGCGGCGACTACTGCGGCAAGGGCTGCCAGAACGGCGCCTGC    WGA-A

146 TACGGGTACTGCGGCATGGGCGGCGACTACTGCGGCAAGGGCTGCCAGAACGGCGCCTGC    WGA-D

154 TACGGGTACTGCGGCATGGGCGGCGACTACTGCGGCAAGGGCTGCCAGAACGGCGCCTGC    BARLEY
                     *

W   T   S   K   R   C   G   S   Q   A   G   G   A   T   C   T   N   N   Q   C
 223 TGGACCAGCAAGCGCTGCGGCAGCCAGGCCGGCGGCGCGACGTGCACCAACAACCAGTGC    WGA-A
                                                         P     H
 206 TGGACCAGCAAGCGCTGCGGCAGCCAGGCCGGCGGGGCGACGTGTCCCAACAACCACTGC    WGA-D
       Y                       T                K     P     H
 214 TACACCAGCAAGCGCTGCGGCACTCAGGCCGGCGGCAAGACATGCCCTAACAACCACTGC    BARLEY
       **            **              ***    *  **  *          *

C   S   Q   Y   G   Y   C   G   F   G   A   E   Y   C   G   A   G   C   Q   G
 283 TGCAGCCAGTACGGGTACTGCGGCTTCGGCGCCGAGTACTGCGGCGCCGGCTGCCAGGGC    WGA-A
                         H   -
 266 TGCAGCCAGTACGGGCACTGCGGCTTCGGAGCCGAGTACTGCGGCGCCGGCTGCCAGGGC    WGA-D
                      W
 274 TGCAGCCAGTGGGGTTACTGCGGCTTCGGCGCCGAGTACTGCGGCGCCGGCTGCCAGGGC    BARLEY
              **  **            *

G   P   C   R   A   D   I   K   C   G   S   Q   A   G   G   K   L   C   P   N
 343 GGCCCCTGCCGCGCCGACATCAAGTGCGGCAGCCAGGCCGGCGGCAAGCTGTGCCCCGAAC   WGA-A
                                                             S
 326 GGCCCCTGCCGCGCCGACATCAAGTGCGGCAGCCAGTCCGGCGGCAAGCTATGCCCCGAAC   WGA-D

334 GGCCCCTGCCGCGCCGACATCAAGTGCGGCAGCCAGGCCGGCGGCAAGCTTTGCCCCAAC   BARLEY
                                                  *        *   *
```

FIGURE 6

```
              N  L  C  C  S  Q  W  G  F  C  G  L  G  S  E  F  C  G  G  G
403 AACCTCTGCTGCAGCCAGTGGGGATTCTGCGGCCTCGGTTCCGAGTTCTGCGGCGGCGGC     WGA-A

386 AACCTCTGCTGCAGCCAGTGGGGATTCTGCGGCCTAGGTTCCGAGTTCTGCGGCGGTGGC     WGA-D
                                     Y                    E
394 AACCTCTGCTGCAGCCAGTGGGGTTACTGCGGCCTCGGCTCCGAGTTCTGCGGCGAGGGC     BARLEY
                *           *  *                          **

C  Q  S  G  A  C  S  T  D  K  P  C  G  K  D  A  G  G  R  V
463 TGCCAGAGCGGTGCTTGCAGCACCGACAAACCGTGCGGCAAGGACGCCGGCGGCAGAGTT     WGA-A

446 TGCCAGAGCGGTGCTTGCAGCACCGACAAGCCGTGCGGCAAGGACGCCGGCGGCAGGGTT     WGA-D
          G                                     A              K
454 TGCCAGGGCGGTGCTTGCAGCACCGACAAGCCGTGCGGCAAGGCCGCCGGCGGCAAAGTT     BARLEY
         *                 *                   *              **

C  T  N  N  Y  C  C  S  K  W  G  S  C  G  I  G  P  G  Y  C
523 TGCACTAACAACTACTGTTGTAGCAAGTGGGGATCCTGTGGCATCGGCCCGGGCTATTGC     WGA-A

506 TGCACTAACAACTACTGTTGTAGCAAGTGGGGATCCTGTGGCATCGGCCCGGGCTATTGC     WGA-D

514 TGCACCAACAACTACTGCTGCAGCAAGTGGGGATCCTGTGGCATCGGCCCGGGCTACTGC     BARLEY
         *    *     *                                          *

G  A  G  C  Q  S  G  G  C  D  G  V  F  A  E  A  I  T  A  N
583 GGTGCAGGCTGCCAGAGTGGCGGCTGCGATGGTGTCTTCGCCGAGGCCATCACCGCCAAC     WGA-A
                    A              G
566 GGTGCAGGCTGCCAGAGCGGCGGCTGTGACGCTGTCTTTGCCGGCGCCATCACCGCCAAC     WGA-D
                                                A
574 GGCGCAGGTTGCCAGAGCGGCGGCTGCGACGGTGTCTTCGCCGAGGCCATCGCCGCCAAC     BARLEY
     *      *       *         *  *   *      **              *

S  T  L  L  Q  E  #  #
643 TCCACTCTTCTCCAAGAATGATGATCAATCTTGCTA  TGGCAGTATT    GCAACGACGAATA  WGA-A
               A
626 TCCACTCTTCTCGCAGAATGATGATCGACCTTCCTA  TGGCAGTATT    GCAACGACGAATA  WGA-D
               V  A
634 TCCACTCTTGTCGCAGAATGATGAT    CTTGCTAATGGCAGTATTATTGCAACGACGAATA  BARLEY
         *  **       ****   *    *              ***

702 ATCCGTGGCAATCTCATTGCCACC  TACGGTTTCCCTTGACTTACTTTTAG AGTA CT     WGA-A

685 ATCCGTGGCAGTTTCATTGCCACGTTACGGTTTCCCTTCACTTACTTTTAGCATTAGCT     WGA-D

693 ATCCGTGGCAGTTTTGTTGCCACG TACGGTCTCCCTTCACTTACTTTTAGCACTAGTC     BARLEY
         *  * **       **       *        *              *  * ***

758 AGTCCTTAATAATTCTCTAGC TTGCAATATGATGTGCAGGTTACTGCAGCAGAAACAAAA     WGA-A

741 AGTACTTAATAATTCTCTAGC TTGCAATGTGACATGCAGGTTACTGCAGCAGAAACAAAA     WGA-D

749     CTTAATAATTCTCCAGCCTTGCAATATGACGTGCAGGTT                     BARLEY
     ****              *   *     *   **         *****************
```

FIGURE 6 (Cont'd)

```
818 TATTGCTGTCGTGCATGCATGGAAATATTGCAGTGAGAAAGTACTGTGTGGCAATATAGG    WGA-A

801 TATTGCTGTGGTACATGCATGGGAATATTGCAGTGAGAAAGTACTGTGTGGCAATATAGG    WGA-D

809         GCTACATGCATGGACATATTGCAGTGAGAA GTACTGTGTGGCAATATAGG    BARLEY
    ********** *               **                   *

878 GTGTGCTATTGTTGCCGCAAATT AGTT   TTCTTGTTA TGACCT    GTTGTCAGGATGC  WGA-A

861 GTGTACTATTGTTGCCGCAAATTTAGTT   TTCTTGTTA TGACCT    GTTGTCAGGATGC  WGA-D

859 GTGTACTATTGTTGCCACAAATTTAGTTCTTTCTTGTTACGTACGTACAGTTGTCAGGATGC  BARLEY
        *         *       *    **          ***  *  ***

933 ATGCATGGCTGTTGTAATGTTGGAGTACTTCGTGATTTCGTTGCAATATAT TA  CCATGGT  WGA-A

917 ATGCATCGCTGTTGTAATGTTGGAGTACTTCGTGATTTCGTTGCAATATAT TA  CCATGAG  WGA-D

921 ATGCATCCCCGTTGTAATGTTGGAGTACTCCATGATTTCGTTGCAATATATATATATTGCCATGAG  BARLEY
         ** *                  * *                   *  ***    **

993 TCTCAC                                                         WGA-A

987 CATCACATCATTAACAAAA                                            WGA-D

985 TCTAAA                                                         BARLEY
    ** * **************
```

FIGURE 6 (Cont'd)

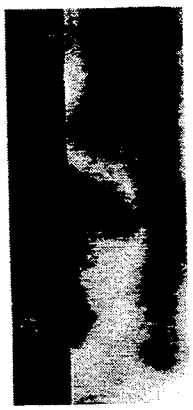
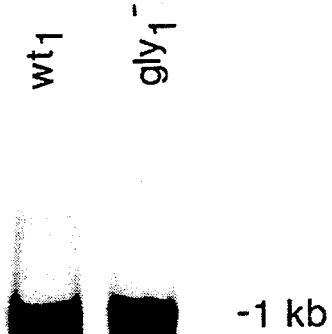
FIG.7A  FIG.7B
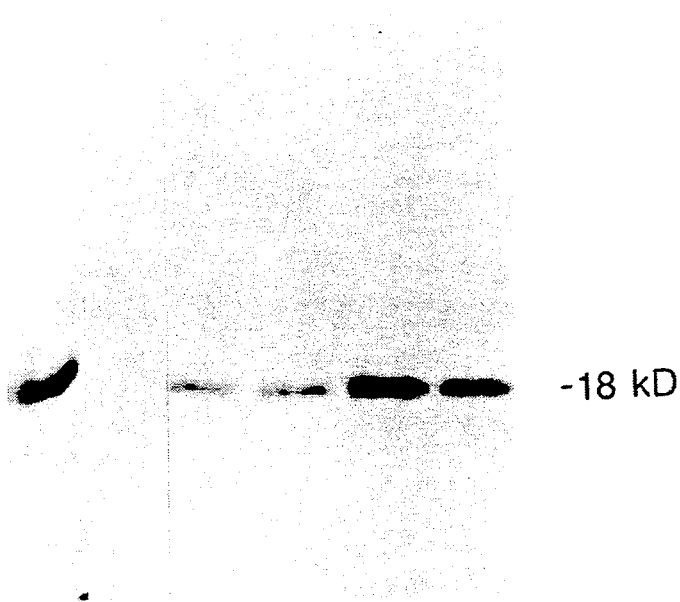
FIG.8

LECTIN CNDA AND TRANSGENIC PLANTS DERIVED THEREFROM

GOVERNMENT RIGHTS

This application was funded under Department of Energy Contract DE-AC02-76ER01338. The U.S. Government has certain rights under this application and any patent issuing thereon.

This is a continuation of copending application Ser. No. 07/406,318 filed on Sep. 12, 1989, now abandoned.

BACKGROUND OF THE INVENTION (1) Field of the Invention

The present invention relates to full length cDNA clones derived from Gramineae, particularly from barley and wheat, and to transgenic plants preferably plants transformed with barley cDNA expressing barley lectin. In particular the present invention relates to transgenic plants which produce an active lectin and store it in leaves and other parts of the plant in amounts which are sufficient to provide insecticidal properties.

(2) Prior Art

It is known that lectins have insecticidal properties. The Gramineae lectins are known to be effective against the cowpea weevil (Murdick et al Phytochemistry 1989). The problem has been to provide these lectins in the leaves and other parts of higher plants for the insects to feed upon. Until the present invention this has not been accomplished, due to the fact that different segments of the DNA of Gramineae which encode the full length of cDNA clones were not available.

OBJECTS

Therefore, it is an object of the present invention to provide full length cDNA's from a Gramineae, preferably barley and wheat. Further, it is an object of the present invention to provide for transgenic higher plants containing the cDNA which produce the lectin and store it in different tissues of the plants. Further still, it is an object of the present invention to provide transgenic plants containing the lectin so as to impart insecticidal properties. These and other objects will become increasingly apparent by reference to the following description and the drawings.

IN THE DRAWINGS

FIG. 1 shows nucleotide and deduced amino acid sequence of barley lectin cDNA clone BLc3. The deduced amino acid sequence is from the first methionine residue and numbered along the right margin. The putative signal sequence, broken underline, and carboxy-terminal extension, double underline, appear not to be present in the mature protein. The single potential asparagine-linked glycosylation site is designated with asterisks. Two stop codons at the end of the coding region are indicated with squares. The four potential polyadenylation signals are underlined. An extensive poly A+tail is not present, so the actual site of polyadenylation is unknown.

FIG. 2 shows in vitro translation and immunoprecipitation analysis of poly A+RNA and BLc3 transcripts. Poly A+RNA isolated from 15 to 25 dpa developing embryos (lane 1) and BLc3 RNA transcripts (lane 2) were translated in vitro using rabbit reticulocyte lysate and $^{35}$S-methionine. Translation products were immunoprecipitated with anti-WGA antiserum, separated on SDS-PAGE and visualized with fluorography. A single product with $M_1$ 21kD was immunoprecipitated in each case indicating BLc3 encodes the barley lectin.

FIG. 3 shows Western blot analysis of native and Endo H treated barley lectin. Isolated barley embryos, 15 to 25 dpa, were treated with 0.1 mM abscisic acid (ABA), a plant hormone, (4 h) to enhance lectin expression. Barley lectin was affinity purified from acid extracted protein and resolved on SDS-PAGE prior to transfer onto nitrocellulose. Western blots were probed with either anti-WGA antiserum, lanes 1 and 2; or anti-WGA-B 172-186, lanes 3, 4 and 5. Anti-WGA-B 172-186 is an antiserum specific for the pro-peptide of pro-WGA. Barley lectin has a $M_1$ 23 kD putative precursor and a $M_1$ 18 kD mature form, lane 1. Commercial WGA, lane 2, contains only the mature lectin, $M_1$ 18 kD. Anti-WGA-B 172-186 detects only the Ml 23 kD pro-barley lectin, lane 3. Treatment for 18 hours at 37° C. with Endo H changes the $M_1$ of pro-barley lectin to $M_1$ 20 kD, lane 4. Anti-WGA-B 172-186 does not detect commercial WGA since no pro-WGA is present, lane 5.

FIGS. 4A to 4D show localization of barley lectin mRNA by in situ hybridization. Barley embryos, 15 to 25 dpa, and root tips from 3-d-old seedlings were cryosectioned to 8 m and probed with BLc3 antisense RNA transcripts. Silver grains developed in the autoradiographic emulsion appear as bright areas with darkfield optics. Phase contrast micrograph of developing embryo, panel 4A, shows the coleorhiza (C), radicles (R), and embryonic root cap (RC). Darkfield micrograph of the same section, panel 4B, localizes barley lectin mRNA in the cells of the coleorhiza, the outer cell layer of the radicle and the root cap. Phase contrast, panel C, and Darkfield, panel 4D, micrographs of root tips from germinating seedlings show specific hybridization of the probe to the root tip and particularly the root cap (RC). Scale bar, 50 m. Magnification, 400X.

FIG. 5 shows Northern analysis of poly A+mRNA from root tips and coleoptiles of 3-d-old and 15 to 25 dpa barley embryos. Poly A+RNA was separated on a formaldehyde/agarose denaturing gel, immobilized on nitrocellulose and hybridized at high stringency with $^{32}$P-labeled cDNA clone BLc3. BLc3 hybridizes to a 1.0 kb mRNA from both embryos, lane 1, and root tips, lane 2. No hybridization to coleoptile poly A+RNA, lane 3, was observed.

FIG. 6 illustrates the complete nucleotide and amino acid sequences of full-length cDNA clones encoding wheat germ agglutinin isolectins A (WGA-A) and D (WGA-D) and barley lectin. Positions with differences in the nucleotide sequence of any of the three sequences are marked with asterisks (*) and the nucleotides are presented in bold-face type. The amino acid sequence derived from translation of WGA-A is shown in one-letter code above the corresponding codon. Amino acids are also indicated at positions where there are differences between the isolectins. As can be seen from FIG. 2, there are significant differences between barley lectin and the wheat germ lectins.

FIGS. 7A and 7B show Southern and Northern blots, respectively, of cDNA constructs in transgenic tobacco.

FIG. 8 shows a Western blot for barley lectin versus a control in a transgenic tobacco plant.

GENERAL DESCRIPTION

Figures 2, 3:

The present invention relates to a cDNA encoding a lectin selected from the group consisting of

```
              M   K   M   M   S   T
  1 ACCAGCACCAAGAAAACAAAAAGCATGAAGATGATGAGCACC                    WGA-A
        M   R
  1 AATAATGAGAAAGATGATGAGCACC                                     WGA-D

1 CAGAAAACAAGAAGGATGAAGATGATGAGCACC                             BARLEY

R   A   L   A   L   G   A   A   A   V   L   A   F   A   A   A   T   A   Q   A
 43 AGGGCCCTCGCGCTCGGCGCGGCTGCCGTCCTCGCCTTCGCCGCGGCGACCGCTCAGGCC  WGA-A
      M   T                   V   F
 26 ATGGCCCTTACGCTCGGCGCGGCTGTCTTCCTCGCCTTCGCCGCGGCGACCGCGCAGGCC  WGA-D
                                                              H
 34 AGGGCCCTCGCTCTCGGCGCGGCCGCCGTCCTCGCCTTCGCGGCGGCGACCGCACGCC    BARLEY
         *   * *       *   *   *           *                    *    *   *

Q   R   C   G   E   Q   G   S   N   M   E   C   P   N   N   L   C   C   S   Q
103 CAGAGGTGCGGCGAGCAAGGCAGCAACATGGAGTGCCCCAACAACCTCTGCTGCAGCCAG  WGA-A

86 CAGAGGTGCGGCGAGCAGGGCAGCAACATGGAGTGCCCCAACAACCTCTGCTGCAGCCAG  WGA-D

94 CAGAGGTGCGGCGAGCAGGGCAGCAACATGGAGTGCCCCAACAACCTCTGCTGCAGCCAG  BARLEY
                   *

Y   G   Y   C   G   M   G   G   D   Y   C   G   K   G   C   Q   N   G   A   C
163 TACGGGTACTGCGGGATGGGCGGCGACTACTGCGGCAAGGGCTGCCAGAACGGCGCCTGC  WGA-A

146 TACGGGTACTGCGGCATGGGCGGCGACTACTGCGGCAAGGGCTGCCAGAACGGCGCCTGC  WGA-D

154 TACGGGTACTGCGGCATGGGCGGCGACTACTGCGGCAAGGGCTGCCAGAACGGCGCCTGC  BARLEY
                     *

W   T   S   K   R   C   G   S   Q   A   G   G   A   T   C   T   N   N   Q   C
223 TGGACCAGCAAGCGCTGCGGCAGCCAGGCCGGCGGCGCGACGTGCACCAACAACCAGTGC  WGA-A
                                                P       H
206 TGGACCAGCAAGCGCTGCGGCAGCCAGGCCGGCGGGGCGACGTGTCCCAACAACCACTGC  WGA-D
      Y               T                       K       P       H
214 TACACCAGCAAGCGCTGCGGCACTCAGGCCGGCGGCAAGACATGCCCTAACAACCACTGC  BARLEY
     * *                   *  *           *   * *   *   * *         *

C   S   Q   Y   G   Y   C   G   F   G   A   E   Y   C   G   A   G   C   Q   G
283 TGCAGCCAGTACGGGTACTGCGGCTTCGGCGCCGAGTACTGCGGCGCCGGCTGCCAGGGC  WGA-A
                       H
266 TGCAGCCAGTACGGGCACTGCGGCTTCGGAGCCGAGTACTGCGGCGCCGGCTGCCAGGGC  WGA-D
                       W
274 TGCAGCCAGTGGGGTTACTGCGGCTTCGGCGCCGAGTACTGCGGCGCCGGCTGCCAGGGC  BARLEY
             *  *  *  *                 *

G   P   C   R   A   D   I   K   C   G   S   Q   A   G   G   K   L   C   P   N
343 GGCCCCTGCCGCGCCGACATCAAGTGCGGCAGCCAGGCCGGCGGCAAGCTGTGCCCCGAC  WGA-A
                                                S
326 GGCCCCTGCCGCGCCGACATCAAGTGCGGCAGCCAGTCCGGCGGCAAGCTATGCCCCGAAC WGA-D

334 GGCCCCTGCCGCGCCGACATCAAGTGCGGCAGCCAGGCCGGCGGCAAGCTTTGCCCCAAC  BARLEY
                                               *                *   *

N   L   C   C   S   Q   W   G   F   C   G   L   G   S   E   F   C   G   G   G
403 AACCTCTGCTGCAGCCAGTGGGGATTCTGCGGCCTCGGTTCCGAGTTCTGCGGCGGCGGC  WGA-A

386 AACCTCTGCTGCAGCCAGTGGGGATTCTGCGGCCTAGGTTCCGAGTTCTGCGGCGGTGGC  WGA-D
                                       Y                     E
394 AACCTCTGCTGCAGCCAGTGGGGTTACTGCGGCCTCGGCTCCGAGTTCTGCGGCGAGGGC  BARLEY
                           *  *           *    *  *                  *  *

C   Q   S   G   A   C   S   T   D   K   P   C   G   K   D   A   G   G   R   V
463 TGCCAGAGCGGTGCTTGCAGCACCGACAAACCGTGCGGCAAGGACGCCGGCGGCAGAGTT  WGA-A

446 TGCCAGAGCGGTGCTTGCAGCACCGACAAGCCGTGCGGCAAGGACGCCGGCGGCAGGGTT  WGA-D
```

```
                 G                            A        K
454 TGCCAGGGCGGTGCTTGCAGCACCGACAAGCCGTGCGGCAAGGCCGCCGGCGGCAAAGTT                BARLEY
                                   *              *         **

C  T  N  N  Y  C  C  S  K  W  G  S  C  G  I  G  P  G  Y  C
523 TGCACTAACAACTACTGTTGTAGCAAGTGGGGATCCTGTGGCATCGGCCCGGGCTATTGC                 WGA-A
506 TGCACTAACAACTACTGTTGTAGCAAGTGGGGATCCTGTGGCATCGGCCCGGGCTATTGC                 WGA-D
514 TGCACCAACAACTACTGCTGCAGCAAGTGGGGATCCTGTGGCATCGGCCCGGGCTACTGC                 BARLEY
         *           *  *                                     *

G  A  G  C  Q  S  G  G  C  D  G  V  F  A  E  A  I  T  A  N
583 GGTGCAGGCTGCCAGAGTGGCGGCTGCGATGGTGTCTTCGCCGAGGCCATCACCGCCAAC                 WGA-A
                       A              G
566 GGTGCAGGCTGCCAGAGCGGCGGCTGTGACGCTGTCTTTGCCGGCGCCATCACCGCCAAC                 WGA-D
                                      A
574 GGCGCAGGTTGCCAGAGCGGCGGCTGCGACGGTGTCTTCGCCGAGGCCATCGCCGCCAAC                 BARLEY
      *       *       *         *    *          **         *

S  T  L  L  Q  E  #  #
643 TCCACTCTTCTCCAAGAATGATGATCAATCTTGCTA TGGCAGTATT    GCAACGACGAATA            WGA-A
                A
626 TCCACTCTTCTCGCAGAATGATGATCGACCTTCCTA TGGCAGTATT    GCAACGACGAATA            WGA-D
          V  A
634 TCCACTCTTGTCGCAGAATGATGAT....CTTGCTAATGGCAGTATTATTGCAACGACGAATA            BARLEY
         *  **                 ****   *    *          ***

702 ATCCGTGGCAATCTCATTGCCACC TACGGTTTCCCTTGACTTACTTTTAG AGTA CT                 WGA-A
685 ATCCGTGGCAGTTTCATTGCCACGTTACGGTTTCCCTTCACTTACTTTTAGCATTAGCT                 WGA-D
693 ATCCGTGGCAGTTTTGTTGCCACG TACGGTCTCCCTTCACTTACTTTTAGCACTAGTC                 BARLEY
             *  ****   **           *       *              *  *  ***

758 AGTCCTTAATAATTCTCTAGC TTGCAATATGATGTGCAGGTTACTGCAGCAGAAACAAAA                WGA-A
741 AGTACTTAATAATTCTCTAGC TTGCAATGTGACATGCAGGTTACTGCACCAGAAACAAAA                WGA-D
749     CTTAATAATTCTCCAGCCTTGCAATATGACGTGCAGGTT................                BARLEY
    ****              *     *          *  **              ****************

818 TATTGCTGTCGTGCATGCATGGAAATATTGCAGTGAGAAAGTACTGTGTGGCAATATAGG                 WGA-A
801 TATTGCTGTGGTACATGCATGGGAATATTGCAGTGAGAAAGTACTGTGTGGCAATATAGG                 WGA-D
809          GCTACATGCATGGACATATTGCAGTGAGAA GTACTGTGTGGCAATATAGG                BARLEY
    ***********  *            **                *

878 GTGTGCTATTGTTGCCGCAAATT AGTT  TTCTTGTTA TGACCT    GTTGTCAGGATGC              WGA-A
861 GTGTACTATTGTTGCCGCAAATTTAGTT  TTCTTGTTA TGACCT    GTTGTCAGGATGC              WGA-D
859 GTGTACTATTGTTGCCACAAATTTAGTTCTTTCTTGTTACGT*ACGTACAGTTGTCAGGATGC              BARLEY
        *            *       **            ***  *  ***

933 ATGCATGGCTGTTGTAATGTTGGAGTACTTCGTGATTTCGTTGCAATATAT TA   CCATGGT             WGA-A
917 ATGCATCGCTGTTGTAATGTTGGAGTACTTCGTGATTTCGTTGCAATATAT TA   CCATGAG             WGA-D
921 ATGCATCCCCGTTGTAATGTTGGAGTACTCCATGATTTCGTTGCAATATATATATTGCCATGAG             BARLEY
        **  *                 *  *                 *  ***        **

993 TCTCAC                                                                       WGA-A

987 CATCACATCATTAACAAAA                                                          WGA-D
```

985 TCTAAA ..............

-continued

The present invention particularly relates to a cDNA encoding barley lectin which comprises: BARLEY

```
                                                                                              M  K  M  M  S  T  R  A  L  A  L  G  A  A  A  V  L  A  F  A     -7
  1   CAGAAAACAAGAAGGAATGAAGATGATGAGCACCAGGGCCCTCGCGCTCGGCGCCGCCGCCGTCCTCGCCTTCGCG

A  A  T  A  H  A  Q  R  C  G  E  Q  G  S  N  M  E  C  P  N  N  L  C  C  S      19
  76  GCGGGCGACCGCGCACGCCCAGAGGTGCGGCGAGCAGGGCAGCAACATGGAGTGCCCCAACAACCTCTGCTGCAGC

Q  Y  G  Y  C  G  M  G  G  D  Y  C  G  K  G  C  Q  N  G  A  C  Y  T  S  K      44
 151  CAGTACGGGTACTGCGGGATGGGCGGCGACTACTGCGGCAAGGGCTGCCAGAACGGCGCTGCTACACCAGCAAG

R  C  G  T  Q  A  G  G  K  T  C  P  N  N  H  C  C  S  Q  W  G  Y  C  G  F      69
 226  CGCTGCGGGCACTCAGGCCGGCGGCAAGACATGCCCTAACAACCACTGCTGCAGCCAGTGGGGTTACTGCGGCTTC

G  A  E  Y  C  G  A  G  C  Q  Q  G  P  C  R  A  D  I  K  C  G  S  Q  A  C      94
 301  GGCGCCGAGTACTGCGGCGCCGGCTGCCAGCAGGGCCCCTGCCGCGCCGACATCAAGTGCGGCAGCCAGGCCTGC

G  K  L  C  P  N  N  L  C  C  S  Q  W  G  Y  C  G  L  G  S  E  F  C  G  E     119
 376  GGCAAGCTTTGCCCCAACAACCTCTGCTGCAGCCAGTGGGGCTACTGCGGCCTCGGCTCCGAGTTCTGCGGCGAG

G  C  Q  G  G  A  C  S  T  D  K  P  C  G  K  A  A  G  G  K  V  C  T  N  N     144
 451  GGCTGCCAGGGCGGCGTGCTTCAGCACCGACAAGCCGTGCGGCAAGGCCGCCGGCGGCAAAGTTTGCACCAACAAC

Y  C  C  S  K  W  G  S  C  G  I  G  P  G  Y  C  G  A  G  C  Q  S  G  G  C     169
 526  TACTGCTGCAGCAAGTGGGGATCCTGTGGCATCGGGCCCGGGTACTGCGGCGCAGGTTGCCAGAGCGGCGGCTGC

D  G  V  F  A  E  A  I  A  A  N  S  T  L  V  A  E  *  *
 601  GACGGTGTCTTCGCCGAGGCCATCGCCGCCAACTCCACTCTTGTCGCAGAATGATGATCTTGCTAATGGCAGTAT

676  TATTGCAACGACGAATAATCCGTGGCAGTTTTGTTGCCACGTACGGTGTGGGTTGAGTTAGTTTTAGCACTAGTC

751  CTTAATAATTCTCCAGCCTTGCAATATGACGTGCTACATGCATGGACATATTGCAGTGAGAAGTACTG

826  TGTGGCAATATAGGGTGTACTATTGTTGCCACAAATTTAGTTCTTTCTTGTTACGTACGTACAGTTGTCAGGATG

901  CATGCATCCCCGTTGTAATGTTGGAGTACTCCATGCATTTCGTTGCAATATATATATTGCCATGAGTCTAAAG
```

Further, the present invention relates to a transgenic plant having leaves containing cDNA encoding a Gramineae lectin stored in the leaves, wherein the lectin provides insecticidal properties to the leaves of the plant.

Cereal lectins are a class of biochemically and antigenically related proteins localized in a tissue-specific manner in embryos and adult plants. To study the specificity of lectin expression, a barley (*Hordeum vulgare* L.) embryo cDNA library was constructed and a clone (BLc3) for barley lectin was isolated. BLc3 is 972 nucleotides long and includes an open reading frame of 212 amino acids. The deduced amino acid sequence contains a putative signal peptide of 26 amino acid residues followed by a 186 amino acid polypeptide. This polypeptide has 95% sequence identity to the antigenically indistinguishable wheat germ agglutinin isolectin-B (WGA-B) suggesting that BLc3 encodes barley lectin. Further evidence that BLc3 encodes barley lectin was obtained by immunoprecipitation of the in vitro translation products of BLc3 RNA transcripts and barley embryo poly A+RNA. In situ hybridizations with BLc3 showed that barley lectin gene expression is confined to the outermost cell layers of both embryonic and adult root tips. On Northern blots, BLc3 hybridizes to a 1.0 kb mRNA in poly A+RNA from both embryos and root tips. On the basis of immunoblot experiments, it appears that barley lectin is synthesized as a glycosylated precursor and processed by removal of a portion of the carboxyl terminus including the single N-linked glycosylation site.

Lectins are a class of proteins with very specific carbohydrate binding properties. Many of the plant lectins are well characterized in their sugar binding specificities and, in some cases, the crystalline structure of the protein is known (Etzler, M. E. Plant lectins: molecular and biological aspects. Ann Rev Plant Physiol 36:209-234 (1985)). In spite of this, the biological significance of plant lectins remains elusive (Etzler, M. E. Plant lectins: molecular and biological aspects. Ann Rev Plant Physiol 36:209-234 (1985)). The Gramineae lectins all specifically bind N-acetylglucosamine and are closely related antigenically and biochemically (Stinissen, H. M., et al., Occurrence and immunological relationships of lectins in gramineous species. Planta 159:105-111 (1983)). These lectins are especially interesting because of their unique patterns of expression in specific cell layers of embryonic organs and in the root tips of adult plants (Mishkind, M. L., etc., Science 220:1290-1292 (1983)).

Lectins from wheat, barley and rye (cereal lectins) are all dimers with 18 kD subunits which are synthesized as 23 kD precursors (Stinissen, H. M., et al, Planta 164:278-286 (1985)). Wheat germ agglutinin (WGA) is the best characterized cereal lectin. Wheat (*Triticum aestivum* L.), however, is a hexaploid with each diploid genome contributing an antigenically indistinguishable isolectin (isolectins A, B and D) (Stinissen, H. M., et al., Planta 159:105-111 (1983)). Functional dimers of WGA isolectins form in vivo by random association of the isolectin monomers (Peumans, W. J., et al., Planta 154:562-567(1982)). Direct sequencing of all three isolectin genes has revealed greater than 90% sequence identity between them (Smith, J. J., et al., Plant Physiol 89S:102 (1989)). These features of the WGA system have made molecular and cellular studies of individual isolectin expression particularly difficult.

The problems with isolectins previously discussed were circumvented by using barley lectin for producing the transgenic plant. Barley, a diploid, contains a lectin shown to be antigenically indistinguishable from WGA (Stinissen, H. M., et al, Planta 159:105-111 (1983)). The lectins are so similar that active heterodimers containing wheat and barley lectin subunits can be formed in vitro (Peumans, W. J., et al., Planta 154:168-572 (1982)). Barley lectin accumulates in the embryonic and adult root tips, but unlike in wheat, rye and rice; no lectin is found in the coleoptile (Mishkind, M. L., et al., J. Cell Biol. 92:753-764 (1982)). By studying lectin expression in barley, the possible complications can be avoided of discerning coleoptile-specific versus root-specific regulatory elements and differential expression of isolectins. A barley lectin cDNA clone, BLc3, was isolated from a barley embryo lambda gt10 library. Using this clone as an in situ hybridization probe lectin mRNA was localized in the embryonic and adult root tips. It appears that the barley lectin precursor is glycosylated and undergoes carboxyl terminal processing to produce the mature polypeptide. A heterologous system was used (transgenic *Nicotiana tabacum* L.) to investigate the molecular mechanisms of post-translational modifications of barley lectin (BLc). Barley lectin is a vacuolar protein that accumulates in the specific cells of developing embryos and in the root tips of adult plants. This lectin undergoes significant post-translational modifications before deposition in the vacuoles: a signal peptide is lost, a high-mannose type oligosaccharide is gained and lost and carboxyl terminal peptide is lost.

The BLc was expressed in tobacco using expression vector pGA643 carrying under control of 35S promoter of CaMV. Site directed mutagenesis and expression of the mutated gene was used in transgenic tobacco to investigate the role of glycans in intracellular trafficking. The BLc was mutated so that the only glycosylation signal on carboxyl-terminus was disrupted to prevent the attachment at asparagine-linked glycan. Under control of 35S promoter, wild type and glycosylation minus constructs accumulates to 0.5% of the total protein in tobacco leaves. Cell fractionation studies and examination by immunocytochemistry show that BLc and BLc without glycan were correctly targeted to the vacuoles of transformed tobacco cells. The biochemical analysis of tobacco BLc indicate that the signal peptide was correctly removed, and that the polypeptide is glycosylated via high mannose glycan at Asn206. The glycan and carboxyl terminal peptide were removed before deposition of the polypeptide in the vacuoles. Furthermore, the absence of high-mannose glycan in the mutated BLc did not alter either the processing of the carboxyl terminal peptide or targeting of the polypeptide to the vacuoles. In both, wild type and glycosylation minus constructs, an active lectin was isolated from transgenic tobacco plants. This system can now be used to identify the vacuolar sorting signal.

The cDNA for WGA, WGD and BLc3 are on deposit at Michigan State University, East Lansing, Mich. The inventor has provided the cDNA to other researchers from the depository.

SPECIFIC DESCRIPTION

(1) Isolation of cDNA

MATERIALS AND METHODS

Plant Material

Barley (*Hordeum vulgare* L. var. Betzes) was grown in soil under growth chamber conditions with a 13 h light cycle (440 E/m²/s) or under greenhouse conditions. Developing grains were harvested at 15 to 25 days post-anthesis (dpa) and stored at −70° C. for RNA isolation or used directly for in situ hybridization and protein extraction. For isolation of root tips and coleoptiles, barley grains were surface sterilized with 10% commercial bleach for 20 minutes, rinsed with sterile distilled water and germinated on Whatman #1 filter paper over 0.7% agar for 3 d.

RNA isolation and Northern blot analysis

Total RNA was isolated from developing embryos and root tips (3 to 5 mm) or whole coleoptiles of 3-d-old seedlings by the method of Finkelstein and Crouch (Finkelstein, R. R., et al, Plant Physiol. 81:907–912 (1986). Polyadenylated RNA (poly A+RNA) was purified by oligo-deoxythymidine (oligo-dT) cellulose affinity chromatography using the method of Silflow et al (Silflow, C. D., et al., Biochem 18:2725–2731 (1979)) except that the poly A+RNA was eluted at room temperature. For Northern analysis, poly A+RNAs were separated electrophoretically, 2 ug per lane, on 2% agarose gels containing 6% formaldehyde and transferred to Immobilon N (Millipore, Bedford, Mass.) as previously described (Raikhel, N. R., et al Proc. Natl. Acad. Sci. USA 84:6745–6749 (1987)). The pre-hybridizations and hybridizations were performed as previously described (Raikhel, N. R., et al., Proc. Natl. Acad. Sci. USA 84:6745–6749 (1987)) except that the amounts of SDS and salmon sperm DNA were increased to 0.1% and 250 ug/ml respectively. The blots were probed with WGA-8 cDNA or BLc3 labeled with $-^{32}$p-ATP by the random primers method (Feinberg, A. P., et al., Anal. Biochem. 132:6–13 (1983)).

Cloning and sequencing a cDNA for Barley Lectin

Poly A+RNA used as a template for cDNA was prepared as described (Mansfield, M. A., et al., Planta 173:482–489 (1988)). The poly A+RNA was examined for lectin mRNA by Northern analysis using a partial cDNA clone for WGA-B (Raikhel, N. V., et al., Proc. Natl. Acad. Sci. USA 84:6745–6749 (1987)) as the probe. The presence of full-length, translatable barley lectin mRNA was demonstrated by in vitro translation followed by immunoprecipitation with anti-WGA antiserum (Mansfield, M. A., et al., Planta 173:482–489 (1988)). The cDNA synthesis reaction was primed with oligo-dT, and the second strand was synthesized using a modification of the Gubler and Hoffman (Gubler, U., et al., Gene 25:263–269 (1983)) method with the Bethesda Research Laboratories (Gaithersburg, Md.) cDNA Synthesis System. The cDNA was ligated into lambda gt10 (Stratagene, San Diego, Calif.) with EcoRI linkers (New England Biolabs, Beverly, Mass.) and packaged in vitro using Gigapack Gold (Stratagene). Plaque forming units (5×10⁵) were screened with $^{32}$-P-labeled WGA-B cDNA at low stringency hybridization conditions (Wilkins, T. A., et al., Plant Cell (in press)) and positive plaques were purified at high stringency (Raikhel, N. V., et al. Planta 176:406–414 (1988)) with the same probe. Inserts from purified plaques were subcloned into the EcoRI site of pUC 119 (Vieira, J., et al., Methods in Enzymology, vol 153:3–11 (1987)) and sequenced by the dideoxynucleotide chain termination method (Sanger, F., et al., Proc. Natl. Acad. Sci USA 74:5463–5467 (1977)) using $-^{35}$S-dATP in place of $-^{32}$P-dATP and 7-deaza-dGTP in place of dGTP (Mizusawa, S., et al., Nucl Acids Res. 14:1319–1324 (1986)). The complete sequence of both strands of one clone, designated BLc3, was obtained by sequencing overlapping deletions generated by T4 DNA polymerase (Dale, R.M.K., et al., Methods in Enzymology, 155:204–214 (1987)). Sequence analysis was performed with Microgenie (Beckman, Fullerton, Calif.) and Editbase software (courtesy of N. Nielsen, Purdue Univ., West Lafayette, Ind.).

In vitro Translations and Immunoprecipitation of BLc3 RNA Transcripts

To generate RNA transcripts, BLc3 was subcloned into the EcoRI site of Bluescript KS+(Stratagene). The construct, designated pBsBLc3, was linearized with XhoI or XbaI for sense or antisense RNA transcripts, respectively. For increased efficiency of translation, "capped" transcripts were generated using an RNA Transcription Kit (Stratagene) according to the manufacturer's protocol with the modifications described below. Capping analog, 0.5 mM m⁷GpppG (Pharmacia, Piscataway, N.J.), and 0.05 mM rGTP were initially used and 2 aliquots of rGTP were added at 10 minute intervals to concentrations of 0.30 mM and 0.55 mM rGTP, respectively.

Two g of "capped" sense transcripts or 10 g barley embryo poly A+RNAs were translated in a rabbit reticulocyte lysate (Promega, Madison, Wisc.) using 50 Ci ³⁵S-methionine (Tran³⁵S-label; ICN Biomedicals, Irvine, Calif.) per reaction. The in vitro translation products were immunoprecipitated (Hondred D., et al., Plant Mol. Biol. 9:259–275 (1987)) using anti-WGA antiserum (Mansfield, M.A., et al., Planta. 173:482–489 (1988)). Samples were carboxyamidated with 2.4 M iodoacetamide at 37° C. for 30 minutes to optimize resolution of the lectins (Raikhel, N.V., et al., Planta. 162:55–61 (1984)). Translation products were analyzed by SDS-PAGE on 12.5% acrylamide gels and visualized by fluorography.

Analysis of Barley Lectin Synthesized In vivo

Barley embryos (300), 15 to 25 dpa, were isolated onto moistened 3MM paper. Embryos were then incubated in 0.1 mM ABA for 4 hours at room temperature to enhance lectin synthesis (Triplett, B. A., et al., Dev. Biol. 91:491–496 (1984)). Acid soluble protein was extracted and affinity-purified on immobilized GlcNAc as previously described (Mansfield, M.A., et al., Planta. 173:482–489 (1988)). Affinity purified lectin, from 100 embryos, was digested with 10 mUnits Endo-beta-N-acetylglucaminidase H (Endo H, Calbiochem, San Diego, Calif.) at 37° C for 18 hours. Samples were lyophilized, carboxyamidated, separated on SDS-PAGE, as above, and electroblotted onto nitrocellulose (Towbin, H., et al., Proc. Natl. Acad. Sci. USA 76:4350–4354 (1979)). Lectin was detected immunologically with anti-WGA antiserum or anti-WGA-B 172–186, an antiserum specific for the 15 amino acid pro-peptide at the carboxyl terminus of pro-WGA (Smith, J. J., et al., Plant Physiol (submitted) (1989)).

In situ Hybridization

For use as in situ hybridization probes, ³⁵S-UTP-labeled sense and antisense RNA transcripts were produced from linearized pBsBLc34. Labeled transcripts were partially hydrolyzed with alkalis to an average size of 150 nucleotides for increased efficiency of hybridization to mRNA in the tissue sections. Barley embryos (15 to 25 dpa) and 3-d-old root tips from growing seedlings were cryosectioned to 8m and processed as previously described (Raikhel, N.V., et al., In situ RNA hybridization in plant tissues. In SB Gelvin, R. A. Schilperoot, eds., Plant Molecular Biology Manual, Sect B9. Kluwer Academic Publishers, Dordrecht, The Netherlands, pp 1-32 (1988)). RESULTS Isolation and characterization of barley cDNA clone BLc3

Eight putative barley lectin clones were isolated from the unamplified barley embryo cDNA library. The 972 nucleotide sequence for one of these clones, designated BLc3 (FIG. 1), was determined from overlapping sequential deletions. BLc3 contains a start codon at nucleotides 16-18 initiating a 212 amino acid open reading frame (calculated mol wt =21,208 D). Amino acid residues $-26$ to $-1$ make up a putative signal sequence (FIG. 1, broken underline). The cleavage site for the signal sequence predicted by the method of von Heijne (von Heijne G., Nucl. Acids Res. 14:4683-4690 (1986)) matches the amino terminus predicted by sequencer identity to mature WGA-B. This putative signal sequence is followed by a 186 amino acid protein with high percentages of Cys (17%) and Gly (22%) and low percentages of His (0.5%), Met (1%), Arg, Ile, Phe, Trp, and Val (1.5% each). A single potential site for Asn-linked glycosylation, Asn-Ser-Thr, is found at residues 206 through 208 (FIG. 1, marked with asterisks). The deduced amino acid sequence of BLc3 is 95% identical to that of WGA-B. Table I lists the amino acid differences between BLc3 and WGA-B.

TABLE I

| Differences in deduced amino acid sequence between barley lectin and WGA-B. | | |
|---|---|---|
| AMINO ACID POSITION | BLc3 | WGA-B |
| Conservative substitutions | | |
| 41 | Tyr | Trp |
| 48 | Thr | Ser |
| 64 | Trp | Tyr |
| 139 | Lys | Arg |
| 179 | Ala | Thr |
| 184 | Val | Leu |
| Non-conservative substitutions | | |
| 9 | Asn | Gly |
| 66 | Tyr | His |
| 123 | Gly | Asn |
| 135 | Ala | Asp |

The coding region is followed by two consecutive TGA termination codons (marked with squares) and a 321 nucleotide 3' untranslated region. Four putative polyadenylation signals (FIG. 1, underlined) are located at positions 688 and 754 (AATAAT), and at positions 832 and (AATATA). Since an extensive poly A+tail is not found however, the exact 3' end of the barley lectin mRNA is To verify that BLc3 encodes barley lectin, BLc3 RNA transcripts and barley embryo poly A+RNA were each translated in vitro. The products were then immunoprecipitated with anti-WGA antiserum and resolved on SDS-PAGE In vitro translation of BLc3 RNA transcripts produced a protein of M121 kD (FIG. 2, lane 1). A $M_1$ 21 kD polypeptide was also specifically immunoprecipitated from in vitro translation products of embryo poly A+RNA (FIG. 2, lane 2). These $M_1$'s agree well with the mol wt of 21.2 kD calculated from the deduced amino acid sequence.

Post-translational modifications of barley lectin

To investigate the in vivo synthesis of barley lectin, Western blots of affinity purified lectin from developing barley embryos were probed with anti-WGA antiserum. Affinity-purified barley lectin contained two polypeptides of $M_1$ 18 kD and $M_1$ 23 kD (FIG. 3, lane 1). Mature barley lectin has the same mobility as purified WGA ($M_1$ 18 kD; FIG. 3, lane 2). The $M_1$ 23 kD protein is most likely the barley lectin precursor (Stinissen, H. M., et al., Planta 164:278-286 (1985)). In vivo labeling studies with barley embryos also show a $M_1$ 23 kD band after immunoprecipitation with anti-WGA antiserum (data not shown). In addition, pulse labeling studies in wheat have shown that WGA is also synthesized as a $M_1$ 23 kD precursor (Mansfield, M.A., et al., Planta. 173:482-489 (1988)). Based on the 95% amino acid sequence identity with WGA-B and the evidence presented above, the $M_1$ 23 kD form is u referred to as the barley lectin precursor. The barley lectin precursor migrates more slowly, $M_1$ 23 kD, on SDS-PAGE than predicted from the deduced amino acid sequence alone (21.2 kD). Since the polypeptide deduced from the clone BLc3 includes the only potential glycosylation site at the carboxy-terminus, it was investigated whether this glycosylation site was utilized. Affinity-purified protein from developing barley embryos was treated with Endo-beta-N-acetylglucaminidase H. Endo H will specifically cleave high mannose oligosaccharides linked to Asn residues. The smaller size of a protein after Endo H digestion would confirm the presence of a high mannose, N-linked glycan. In this experiment an antiserum specific for the carboxyl-terminal portion of pro-WGA, anti-WGA-B 172-186 (Smith, J. J., et al., Plant Physiol., (submitted (1989)) was used. Binding of anti-WGA-B 172-186 to pro-barley lectin was expected since there are only 2 conservative amino acid differences between the pro-peptide of WGA-B and the last 15 residues encoded by BLc3 (Table I) Anti-WGA-B 172-186 detected the $M_1$ 23 kD precursor band but failed to recognize mature barley lectin in the sample (FIG. 3, lane 3). This provides further evidence that the $M_1$ 23 kD band represents pro-barley lectin. Endo H digestion of affinity-purified barley lectin reduced the size of pro-barley lectin by $M_1$ 3 kD (FIG. 3, lane 4), indicating the presence of a high-mannose oligosaccharide.

Cellular localization and temporal expression of barley lectin

Figure 4A:
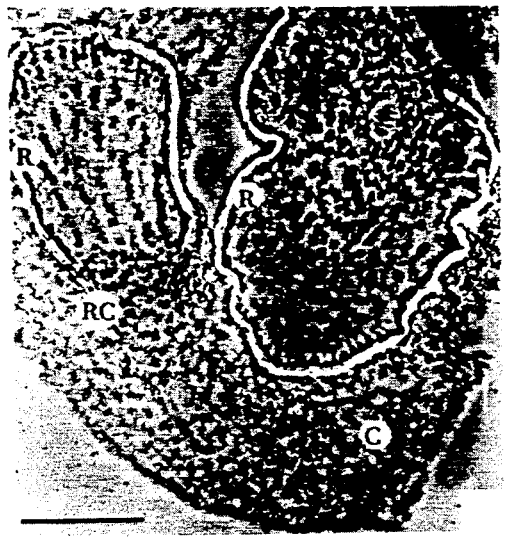
Figure 4B:
Figure 4C:
Figure 4D:
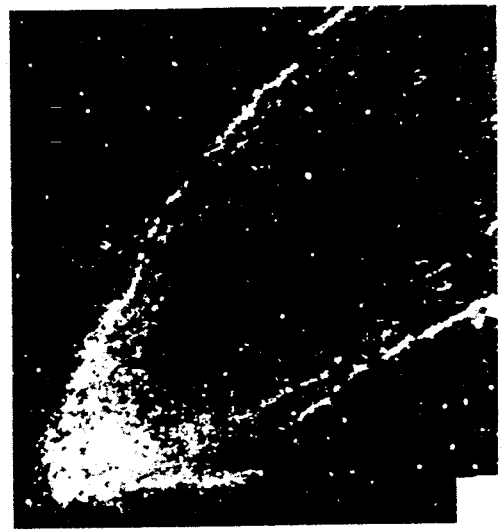

The spatial distribution of barley lectin mRNA was determined by in situ hybridization with BLc3 antisense RNA transcripts. Barley lectin mRNA was localized to the coleorhiza, outer cell layers of the radicles, and the root caps of the developing embryo (FIG. 4a and b). Lectin mRNA was also found in the root tip and root cap of 3-d-old seedlings (FIG. 4c and d). Lectin mRNA was not detected in the primordial leaves, coleoptile or scutellum of the embryo (data not shown). Sense BLc3 RNA transcripts, used to monitor non-specific binding of labeled nucleic acids to the sections, did not bind significantly to any tissue (data not shown).

Figure 5:
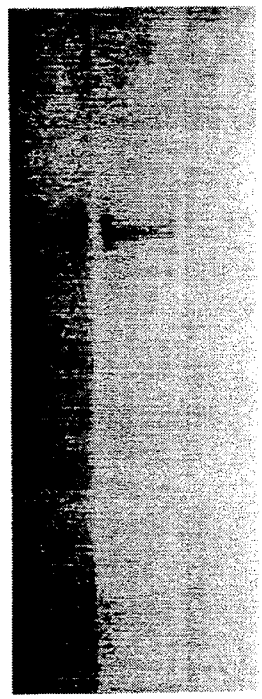

To determine if barley lectin mRNAs from embryos and adult roots were the same size, Northern blot analysis was performed (FIG. 5). A 1.0 kb mRNA was detected in poly A+RNA from both tissues (FIG. 5, lanes 1 and 2). No detectable lectin mRNA was found in coleoptiles of 3-d-old seedlings (FIG. 5, lane 3).

The first goal was to gain an understanding of the mechanisms controlling the specificity of expression observed in the cereal lectins. Previous work showed that de novo synthesis of both lectin mRNA (Raikhel, N. V., et al, Planta. 176:406-414 (1988)) and protein (Raikhel, N.V, et al., Planta. 162:55-61 (1984)) is responsible, at least in part, for the pattern of accumulation seen for WGA expression. These data suggest that transcriptional control accounts for some of the observed specificity. The pattern of lectin expression found in cereals is species specific. However, only barley lectin is expressed solely in the adult and embryonic roots. As an initial site in understanding this root-specific expression, a cDNA clone for barley lectin, BLc3, was isolated and characterized.

Complementary DNA clone BLc3 encodes barley lectin

BLc3 was shown to encode barley lectin by in vitro translation experiments followed by immunoprecipitation of the products. As shown previously, barley lectin and WGA are immunologically indistinguishable (Stinissen, H. M., et al., Planta. 159:105-111 (1983)). Thus, anti-WGA antiserum should immunoprecipitate in vitro translation products of BLc3. The results herein show a Ml 21 kD polypeptide was immunoprecipitated by anti-WGA antiserum. These data were supported by in vitro translation and immunoprecipitation of barley embryo poly A+RNA. Here, a single $M_1$ 21 kD band was also immunoprecipitated by anti-WGA antiserum. The identical $M_1$ of the immunoprecipitated products from both sources indicates that BLc3 probably contains the entire coding region of barley lectin.

Analysis of the amino acid sequence encoded by BLc3 provides further evidence that BLc3 encodes barley lectin. The amino acid composition, rich in Gly and Cys while poor in several other amino acids, is characteristic of the cereal lectins (Peumans, W. J., et al., Biochem. J 203:239-243 (1982)). In addition, there were only 10 differences (95% sequence identity) between WGA-B and the deduced amino acid sequence of barley lectin (Table I). Six of these differences were conservative substitutions (Microgenie, Beckman); making the structural similarity even greater. The striking sequence identity found between BLc3 and WGA-B explains the immunological similarity (Stinissen, H. M., et al., Planta 159:105-111 (1983)) and the agglutinating activity of WGA/barley lectin heterodimers (Peumans, W. J., et al. Planta 154:568-572 (1982)).

The translated sequence of BLc3 is given from the first methionine codon. It is unknown, however, which of the initial methionine residues (−26, −24 or −23) is used to initiate translation in vivo. The coding region of BLc3 begins with a typical tripartite signal sequence (residues −26 to −1) characteristic of secretory proteins. This signal sequence was expected in a full length clone since previous studies have localized cereal and rice lectins to the vacuoles/protein bodies (7, 8, 24). The predicted cleavage site (von Heijne, G., Nucl. Acids Res. 14:4683-4690 (1986)) for the signal sequence corresponds exactly to the amino terminus of mature WGA. These data support the hypothesis that Gln #1 is the amino-terminus of the mature barley lectin although the actual terminus is unknown.

Glycosylation and cleavage of a pro-peptide from pro-barley lectin

The results presented in this invention shows that the precursor for barley lectin ($M_1$ 23 kD) is larger than predicted from the cDNA sequence (mol. wt. 21.2 kD). Pro-barley lectin was found to be Endo H sensitive and therefore glycosylated with a high mannose glycan. This glycan accounts for only part of the additional size of the precursor. In these experiments a polyclonal antiserum, anti-WGA-B 172-186, specific for pro-WGA was used (Smith, J. J., et al., Plant Physiol., (submitted) (1989)).

Anti-WGA-B 172-186 specifically recognized pro-barley lectin and deglycosylated pro-barley lectin, but did not find mature barley lectin. This makes anti-WGA-B 172-186 an especially powerful tool for investigating modifications of the carboxyl-terminal end of barley lectin. The results of these experiments is to tentatively assign the carboxyl-terminus of mature barley lectin as Gly #171, although the actual terminal residue is unknown. Furthermore, mature barley lectin has the same $M_1$ as WGA on SDS-PAGE and the region surrounding the carboxyl-terminus of mature WGA is identical in barley lectin (Table I).

Thus, based upon the results with anti-WGA-B 172-186 and sequence identity with WGA-B, the carboxyl terminal portion of the barley lectin precursor (double underlined in FIG. 1) is probably absent in mature barley lectin. WGA (Mansfield, M. A., et al., Planta 173:482-489 (1988), rice lectin (Wilkins, T. A., et al., Plant Cell (in press) (1989)) and beta-glucanase (Shinshi, H., et al., Proc. Natl. Acad Sci. USA 85:5541-5545 (1988)), have also been shown to be synthesized as glycosylated precursors and undergo carboxyl-terminal processing of the polypeptide.

Temporal and cellular localization of barley lectin

In situ hybridization experiments show barley lectin mRNA is localized to the root tip of the adult plant and the analogous structures in the embryo. As might be expected, this pattern of expression coincides with that for lectin accumulation (Mishkind, M. L., et al., Science 220:1290-1292 (1983)). WGA-B mRNA shows a similar pattern of expression (Raikhel, N.V., et al. Planta 176:406-414 (1988)), however, recent data showing greater than 90% identity between wheat isolectin mRNAs (Smith, J. J., et al., Plant Physiol. 89S:102 (1989)) will make precise analysis of individual isolectin expression difficult. Furthermore, the complicated pattern of WGA accumulation in different genotypes of wheat remains unexplained (Raikhel, N.V., et al., In TC Bog-Hansen, E van Driessche, eds., Lectins, Vol. V, Walter de Gruyter & Co., Berlin pp. 75-81 (1986)). The barley lectin system, devoid of isolectin complications, is therefore superior for the study of root tip-specific protein expression. The cDNA for barley lectin presented of the present invention provides a valuable tool for the isolation of gene promotor sequences for barley lectin and characterization of the cis-elements involved in root-tip-specific expression.

(2) Transgenic Plant

Materials and Methods

Modification of barley lectin cDNA Flanking Regions

The 972 bp EcoRI insert from pBLc3 encoding barley lectin (Lerner and Raikhel, Plant Physiol. 90 (in press) (1989)) was blunt-ended with DNA Polymerase I Klenow fragment and XbaI linkers (BRL) added to the flanking regions of the cDNA (Maniatis, et al., Molecular Cloning: A Laboratory Manual (1982)). The cDNA was subcloned into pUC118 (Vierira and Messing, Methods Enzymol. 153, 3-11 (1987)) from low-melting point agarose according to Struhl (Struhl, K., Biotechniques 3, 452-453 (1985)) and screened for the anti-sense orientation. Restriction mapping of the cDNA revealed that the EcoRI sites originally flanking the barley lectin cDNA were restored by the addition of XbaI linkers.

Site-directed Mutagenesis

The N-linked glycosylation site at $Asn_{206}$-Ser-Thr in the COOH-terminal glycopeptide of the barley lectin proprotein (Lerner, D. R., et al., Plant Physiol. 90 (in press) (1989)) was inactivated by the conversion of $Asn_{206}$ (AAC) to a Gly (GGC) residue by the site-directed mutagenesis method of Kunkel, et al. (Kunkel, T. A., et al., Methods Enzymol. 154: 367-382 (1987)). Site-directed mutagenesis was performed using Bio-Rad's Muta-Gene phagemid in vitro mutagenesis kit with a 16-base synthetic oligonucleotide spanning amino acids 204 to 208 (Lerner and Raikhel, Plant Physiol. 90, Plant Physiology 91, 124-129 (1989) (1989)) and uracil-containing single-strand DNA prepared in the dut-ung- *E. coli* strain CJ236. Mutants containing sequences encoding the tripeptide Gly-Ser-Thr were identified and selected by sequencing single-strand DNA prepared from phagemids in the dut+ung+*E. coli* strain MV1193 by the dideoxy chain termination method (Sanger, et al., Proc. Natl. Acad. Sci. USA 56:5463-5467 (1977)).

The gene sequences are maintained on computer by Genebank, Los Alamos, N. Mex. as follows:
Barley Accession No. 24846;
WGA-A Accession No. M25536; and
WGA-D Accession No. M25537.

Plant Transformation

Both mutated (gly-) and wild-type (wt) barley lectin cDNAs were excised from pUC118 with XbaI and subcloned (Struhl, K., Biotechniques 3:452-453 (1985)) into the binary plant expression vector pGA643 (An, et al., Plant Molec. Biol. Manual A3, 1-19 (1988)). These binary vector constructs were mobilized from the *E. coli* strain DH5 alpha into *Agrobacterium tumefaciens* LBA4404 (An, previously cited) by triparental mating (Hooykaas, P. J. J., Plant Molec. Biol. Manual A4, 1-13 (1988)) using the *E. coli* strain HB101 harboring the wide-host range mobilizing plasmid pRK2013 (Clonetech, Palo Alto, Calif.). Transconjugates were selected on minimal nutrient plates (An, G., et al., Plant Molec. Biol. Manual A3, 1-19 (1988)) containing Kanamycin (5 ug/ml) and tetracycline (12.5 ug/ml).

Agrobacterium cells containing the wt and gly-barley lectin constructs were introduced into tobacco plants (*Nicotiana tabacum* cv. Wiconsin 38) by the leaf disc transformation method of Horsch, et al. (Horsch, R. B., et al., Plant Molec. Biol. Manual A5, 1-9 (1988)). The leaf discs were incubated for 48 hours on MS agar prior to transfer to shooting media (MSA media containing 150 ug/ml kanamycin and 500 ug/ml carbenicillin). After several weeks, shoots were transferred to rooting media (MS media) in the presence of 150 ug/ml kanamycin and 500 ug/ml carbenicillin. At least three independent transformants, maintained as axenic cultures, were subsequently analyzed for each construct.

Nucleic Acid Anaysis

Total DNA was isolated from leaf tissue of untransformed and transgenic tobacco plants according to Dellaporta, et al. (Dellaporta, S. L., et al., Plant Molec. Biol. Rep. 1:19-21 (1983)). DNA (15 to 20 ug) was restricted with EcoRI or HIndIII and fractionated on 0.8% agarose gels prior to transfer to nitrocellulose (Maniatis, et al., Molecular Cloning: A Laboratory Manual (1982)). Nitrocellulose filters were hybridized with $^{32}P$ random-primer-labeled (Feinberg and Vogelstein, Anal. Biochem. 132: 6-1 (1983)) BLc3 barley lectin cDNA (Lerner and Raikhel, Plant Physiol. 90, (in press) (1989)) as described previously (Raikhel, et al., Planta 126: 406-414 (1988)). For gene reconstruction analysis, BLc3 was titered at 0.5-, 1.0-, 3.0- and 5.0- copies per haploid genome of N. tabacum. Filters were exposed to Kodak X-OMAT AR film at $-80°$ C. with intensifying screens.

Total RNA was isolated from leaves of untransformed and transgenic tobacco plants as described previously (Wilkins and Raikhel, The Plant Cell 1:541-549 (1989)). Total RNA (25 ug) from each construct was resolved in a 2% agarose/6% formaldehyde gel, transferred to nitrocellulose, and hybridized (Raikhel, et al., Planta 126:406-414 (1988)) with the BLc3 cDNA (Lerner and Raikhel, [Plant Physiol. 90 (in press) (1989)) labeled with 32P as described above.

Protein Extraction, Affinity Chromatography, and Immunoblots

Barley lectin was purified from acid soluble proteins extracted from transgenic tobacco leaves (500 mg) by affinity chromatography on immobilized N-acetylglucosamine affinity columns essentially as described in Mansfield et al. (Mansfield, M.A., et al., Planta 173:482-489 ((1988)) with the exception that the homogenization buffer consisted of 50 mM HCL containing 1 mM phenylmethylsulfonyl fluoride. The affinity-purified lectin was carboxyamidated (Raikhel, et al., Planta 162:55-61 (1984)) fractionated by SDS-PAGE (Mansfield, et al., Planta 173:482-489 (1988)), and electroblotted onto mitrocellulose (Towbin, et al., 1979). Barley lectin was detected using anti-WGA polyclonal antiserum (Mansfield, M. A., et al., Planta 173:482-489 (1988)) and protein A-alkaline phosphatase as described in Blake, et al. (Blake, M., et al., Anal. Biochem. 136:175-179 (1984)) and nitroblue tetrazolium as the substrate.

Radiolabeling of Tobacco Protoplasts and EndoH Digestion

Protoplasts for labeling were prepared from fully expanded leaves of axenic cultured plants. Leaves were digested overnight in an enzyme mixture comprised of 0.5% cellulase (Onozuka R10), 0.25% macerozyme R10, and 0.1% BSA in MSA media (An, et al., Plant Molec. Biol. Manual A3, 1-19 (1988)) 1/mg/1 NAA and 0.1 mg/1 BA supplemented with 0.5 M mannitol. Protoplast yield was quantitated using a hemocytometer counting chamber.

For labeling experiments, 1 x 105 leaf protoplasts per well were incubated in a 24 well Falcon tissue culture plate in 500 ul MS 1 mg/1 NAA 0.1 mg/1 BA supplemented with 48 uCi of $L-^{35}S$-methionine in the dark at room temperature with gentle shaking. Two wells or a total of 200,000 protoplasts were labeled for each experiment. Samples were collected at timed intervals over a 24 hour period or for 12 hours. Following labeling, protoplasts were pooled and collected by centrifugation at 4° C. 2 krpm for 15 seconds. The resulting protoplast pellet was suspended in 100 ul of 50 mM Tris-acetate, 100 mM NaCl, pH 5.5 and lysed at room temperature for 10 minutes with gentle agitation following the addition of 100 ul of 1.2 mM dithiothreitol and 1.2% (vv) Triton X-100 in Tris-acetate/NaCl. Samples were frozen in liquid $N_2$ and stored t $-70°$ C. Following collection of protoplasts by centrifugation, the incubation media was recovered and contaminating intact protoplasts removed by gravity filtration through a Isolab quick-sep column containing a paper filter and a Whatman GF/C glass fiber filter. Proteins contained in the medium were precipitated with $(NH_4)_2SO_4$ at 60% saturation for at least 2 hours at 4° C. Precipitated proteins were collected by centrifugation at 15 krpm at 4° C. The protein pellet was subsequently treated and stored as described for the protoplast pellet described above.

35S-labeled barley lectin was purified by affinity chromatography and analyzed by SDS-PAGE as described above. The SDS-PAGE gels were treated for fluorography as detailed in Mansfield et al (Mansfield, M.A., et al., Planta 173:482–489 (1988)).

EndoH digestions of affinity purified $^{35}$S-labeled barley lectin were performed according to Trimble and Maley (Trimble, R. B., et al., Anal. Biochem. 141:515–522 (1984)).

Vacuole Isolation and Enzyme Assays

Protoplast for vacuole isolation were prepared from leaves of axenic cultured plants. Leaves were digested overnight in an enzyme medium composed of 0.5 M mannitol and 3 mM MES, pH 5.7 containing the same enzymes as described above. Vacuoles were isolated from tobacco protoplasts by ultracentrifugation as described in Guy et al (Guy, M., et al., Plant Physiol. 64:61–64 (1979)) with the exception that the isolation buffer was 0.5 M sorbitol and 10 mM HEPES, pH 7.2 and the Ficoll step gradient consisted of 10% and 5% Ficoll. A second step gradient was also included to enhance purity of vacuoles. The vacuoles recovered were counted in a hemocytometer, frozen in liquid nitrogen, and stored at $-80°$ C. for biochemical analysis.

Vacuolar-specific enzyme activities of a-mannosidase (Boller, T., et al., Plant Physiol. 63:1123–1132 (1979)) and acid phosphatase (Shimomura, S., et al., Planta 175:558–566 (1988)) were assayed in protoplast and vacuole fractions by monitoring the release of p-nitrophenol spectrophotometrically from the appropriate substrates.

Immunocytochemistry

Leaf tissue from axenic tobacco plants was excised and trimmed into 2 mm$^2$ pieces. Fixation and immunocytochemistry was performed essentially as described in Mansfield et al (Mansfield, M. A., et al., Planta 173:482–489 (1988)).

Results

Inactivation of N-linked Glycosylation Site of Barley Lectin Preproprotein by Site-Directed Mutagenesis.

To assess the possible functional role of the high mannose N-linked glycan in the assembly and post-translational processing of the pro-barley lectin to the mature polypeptide, site-directed mutagenesis was performed to inactivate the N-linked glycosylation site. A mutagenic oligonucleotide primer was synthesized to complement the barley lectin coding region spanning the Asn$_{206}$-Ser-Thr$_{208}$ glycosylation site within the COOH-terminal propeptide. This oligonucleotide primer eliminates the N-linked glycosylation site Asn-Ser-Thr by converting Asn206 to a Gly residue.

Both the wild-type and mutated barley lectin cDNA clones, designated wt$^-$ and gly$^-$, respectively, were cloned behind the CaMV 35S promoter in the binary plant transformation vector pGA643 (An, et al., 1988). Each construct was transformed into Nicotiana tabacum cv. W 38 by the leaf disc method of Horsch, et al (1988). At least three kanamycin-resistant plants were analyzed for each construct.

DNA and RNA analysis of barley lectin in transgenic tobacco.

The structure and stable transformation of wt and gly$^-$barley lectins into the tobacco genome was ascertained by Southern blot analysis of independent transformants for each construct. A representative Southern blot containing genomic DNA (20 ug) restricted with HindIII is shown in FIG. 7A. Restriction of genomic DNA with HindIII releases a 380-bp fragment representing the 5'-terminal sequences of barley lectin cDNA in both constructs. The remaining 592 bp of the barley lectin cDNA, the right border of the T-DNA, and flanking regions of tobacco DNA are evident as a single 2.8 kb fragment in wt transformants and as two fragments of 2.8 and 2.5 kb in the gly$^-$transformants. Similar results were obtained with BamHI (data not shown). To further ascertain the number of barley lectin cDNAs integrated into the tobacco genome, gene reconstruction experiments (FIG. 7A) were conducted with EcoRI-restricted genomic DNA and purified pBLc3 barley lectin cDNA insert titered at 0.5-, 1.0-, and 3.0-copies per tobacco haploid genome. The results of the reconstruction experiment (FIG. 7B) demonstrated that the wt constructs contain one-copy of barley lectin per haploid genome whereas the gly$^-$transformants typically contain 2-copies of the barley lectin cDNA integrated into the tobacco genome. No hybridization was observed with DNA isolated from non-transformed tobacco (Lane ctl, FIG. 7A).

FIG. 8 shows immunoblots of barley lectin purified by affinity chromatography from acid soluble extracts of tobacco transformants were performed to determine if this monocot protein is assembled into an active lectin in a heterologous system.

The relative levels of mRNA corresponding to the wt and gly$^-$barley lectin contructs in transgenic tobacco was examined by Northern blot analysis. FIG. 8 shows the accumulation of steady-state mRNA of wt and gly$^-$barley lectin in total RNA isolated from transgenic tobacco leaves and hybridized with $^{32}$P-labeled pBLc3 barley lectin cDNA. Two mRNA species of 1.0 and 0.8 kb were identified in tobacco containing either the wild-type or mutant barley lectin constructs (Lanes wt$_1$ and gly$_1$, respectively, FIG. 7B). The 1.0 kb barley lectin mRNA corresponds in length to the mRNA encoding barley lectin in developing barley embryos (Lerner and Raikhel, 1989). The 0.8 kb mRNA species is unique to transgenic tobacco plants and presumably represents utilization of an alternate polyadenylation site contained within the 3'-untranslated region of the barley lectin cDNA (Lerner and Raikhel, 1989). While the 1.0 kb mRNA species accumulates to similar levels in tobacco containing both constructs, the 0.8 kb mRNA is approximately 2- to 3-fold more abundant in plants containing the wt construct (Lane wt$_1$, FIG. 8) than the gly$^-$construct (Lane gly$^-$, FIG. 8) in these particular transformants. No hybridization was observed in the untransformed tobacco control (Lane ctl., FIG. 8). The accumulation of similar levels of lectin mRNA in tobacco, transformants containing the wt or gly$^-$barley lectin constructs does not reflect the number of copies of the barley lectin cDNA integrated into the tobacco genome as determined by gene reconstruction analysis (FIG. 7A). The disparity between the level of expression and the number of copies of the cDNA contained within the tobacco genome may reflect a positional effect such that 1-copy of the gly$^-$cDNA is not transcribed or both copies of the gly$^-$cDNA in the tobacco genome are transcribed less efficiently than the transformant containing the wt cDNA.

Figure 9:
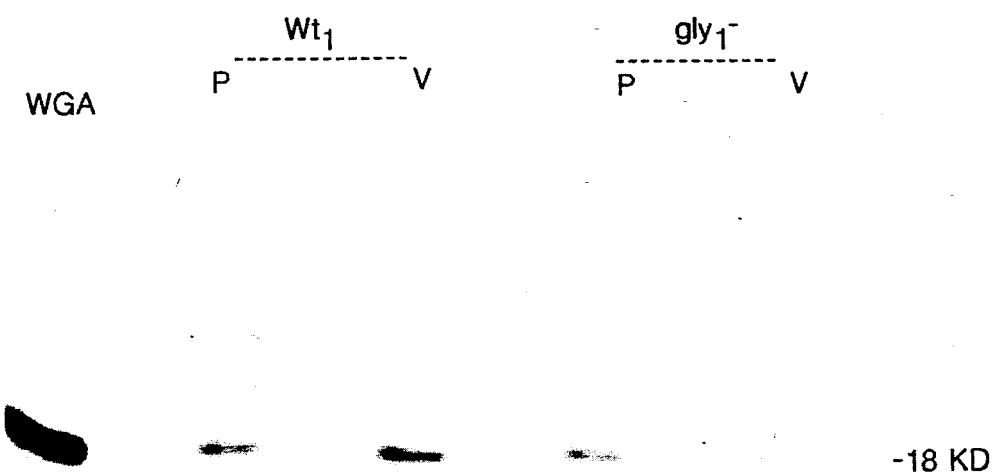
FIG. 9 shows a Western blot for barley lectin isolated from vacuoles and protoplasts of transgenic tobacco plants.
Figure 10A:
FIGS. 10A to 10C shows immunochemical localization of glycosylation mutant of barley lectin in the vacuoles of tobacco mesophyll cells (FIGS. 10A and 10B) and in vacuoles of developing barley embryos (FIG. 10C).
Figure 10C:
Figure 10B:
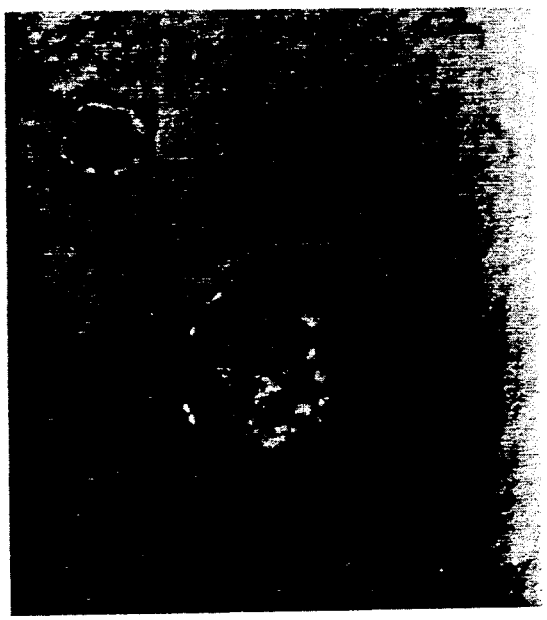

FIGS. 9 and 10 show and confirm the localization of the barley lectin in the vacuoles of mesophyl cells. Using vacuolor purification and electron microscopy immunocytochemistry (antibodies against lectin with a colloidal gold label).

It was concluded that (1) Barley lectin, which is expressed in specific cells of embryos and in the root caps of adult plants, is correctly processed and targeted to the vacuoles of transformed tobacco cells; and (2) Active lectin is produced in the transformed tobacco cells.

It is intended that the foregoing description be only illustrative of the present invention and that the present invention be limited only by the hereinafter appended claims.

I claim:

1. A transgenic plant comprising a cDNA of a Gramineae lectin selected from the group consisting of barley BLc3, wheat WGA-A or wheat WGA-D in which said cDNA is non-native to said plant and is expressed in quantities sufficient to provide insecticidal properties in the leaves of said plant.

2. The plant of claim 2 wherein the cDNA is

```
                                                                                                                    -7
   1                                                         M  K  M  M  S  T  R  A  L  A  L  G  A  A  A  V  L  A  F  A
         CAGAAAACAAGAAGGATGAAGATGATGAGCACCAGGGCCCTCGCTCTCGGCGCCGCCGCCGTCCTCGCCTTCGCG

A  A  T  A  H  A  Q  R  C  G  E  Q  G  S  N  M  E  C  P  N  N  L  C  C  S                      19
  76     GCGGCGACCGCGCACGCCCAGAGGTGCGGCGAGCAGGGCAGCAACATGGAGTGCCCCAACAACCTCTGCTGCAGC

Q  Y  G  Y  C  G  M  G  G  D  Y  C  G  K  G  C  Q  N  G  A  C  Y  T  S  K                      44
 151     CAGTACGGGTACTGCGGCATGGGCGGCGACTACTGCGGCAAGGGCTGCCAGAACGGCGCTGCTACACCAGCAAG

R  C  G  T  Q  A  G  G  K  T  C  P  N  N  H  C  C  S  Q  W  G  Y  C  G  F                      69
 226     CGCTGCGGCACTCAGGCCGGCGGCAAGACATGCCCTAACAACCACTGCTGCAGCCAGTGGGGTTACTGCGGCTTC

G  A  E  Y  C  G  A  G  C  Q  G  G  P  C  R  A  D  I  K  C  G  S  Q  A  C                      94
 301     GGCGCCGAGTACTGCGGCGCCGGCTGCCAGGGCGGCCCCTGCCGCGCCGACATCAAGTGCGGCAGCCAGGCCGGC

G  K  L  C  P  N  N  L  C  C  S  Q  W  G  Y  C  G  L  G  S  E  F  C  G  E                     119
 376     GGCAAGCTTTGCCCCAACAACCTGTGCTGCAGCCAGTGGGGCTACTGCGGCCTCGGCTCCGAGTTCTGCGGGGAG

G  C  Q  G  G  A  C  S  T  D  K  P  C  G  K  A  A  G  G  K  V  C  T  N  N                     144
 451     GGCTGCCAGGGCGGTGCTTGCAGCACCGACAAGCCGTGCGGCAAGGCCGCCGGCGGCAAAGTTTGCACCAACAAC

Y  C  C  S  K  W  G  S  C  G  I  G  P  G  Y  C  G  A  G  C  Q  S  G  G  C                     169
 526     TACTGCTGCAGCAAGTGGGGATCCTGTGGCATCGGGCCCGGCTACTGCGGCGCCGGCTGCCAGAGCGGGGGCTGC

D  G  V  F  A  E  A  I  A  A  N  S  T  L  V  A  E  *  *
 601     GACGGGGTGTCTTCGCCGAGGCCATGCCGCCAACTCCACTCTTTGTCGCAGAATGATGATCTTGCTAATGGCAGTAT

676     TATTGCAACGACGAATAATCCGTGGCCAGTTTGTTGCCACGTACGGTTGTGGGTTGAGTTAGTTTTAGCACTAGTC

751     CTTAATAATTCTCCAGCCTTGCAATATGACGTGCAGGTTGCTACATGCATGGACATATTGCAGTGAGAAGTACTG

826     TGTGGCAATATAGGGTGTACTATTGTTGCCACAAATTTAGTTCTTTCTTGTTACGTACGTACAGTTGTCAGGATG

901     CATGCATCCCCGTTGTAATGTTGGAGTACTCCATGATTTCGTTGCAATATATATATATTGCCATGAGTCTAAAG
```

3. The plant of claim 2 which is a tobacco plant.

4. The plant of claim 1 wherein the lectin is particularly stored in vacuoles in the leaves of the plant as well as other tissue of the plant.

5. The plant of claim 1 wherein the cDNA is transformed from *Agrobacterium tumefaciens* to leaf samples of the plant and then the leaves are grown to produce the plant from the sample.

6. The plant of claim 5 wherein the *Agrobacterium tumefaciens* is LBA strain 4404.

7. The plant of claim 5 wherein in a triparental mating the cDNA was cloned into a plant vector PGA 643 in a first *E. coli* which was then transferred to the *Agrobacterium tumefaciens* LBA 4404 using a second *E. coli* containing a pK 2013 vector for the cDNA and wherein the cDNA has been transformed into the samples of the plant by the *Agrobacterium tumefaciens*.

8. The plant of claim 5 wherein the second *E. coli* is HB101 containing the vector.

9. The plant of claim 1 wherein the cDNA is barley BLc3.

10. The plant of claim 1 wherein the cDNA is wheat WGA-A.

11. The plant of claim 1 wherein the cDNA is wheat WGA-D.

* * * * *

UNITED STATES PATENT AND TRADEMARK OFFICE
CERTIFICATE OF CORRECTION

PATENT NO. : 5,276,269
DATED : January 4, 1994
INVENTOR(S) : Natasha V. Raikhel

It is certified that error appears in the above-indentified patent and that said Letters Patent is hereby corrected as shown below:

Title page, under [56] "Other Publications", line 1, "Vaecd" should be --Vaeck--.

Title page, column 2, line 30, "Peumens" should be --Peumans--.

Column 2, line 16, "M1 23 kD" should read --$M_l$ 23 kD--.

Column 13, line 33, "WGA-8" should be --WGA-B--.

Column 15, line 50, after "and" and before "(AATATA)", --946-- should be inserted.

Column 15, line 52, after "is", --unknown.-- should be inserted.

Column 15, line 57, after "SDS-PAGE", a period --.-- should be inserted.

Column 15, line 58, "M121" should be --$M_l$21--.

Column 16, line 13, before "referred", "u" should be deleted.

Column 16, line 39, "$M_l$ 3 kD" should be --$M_l$ 23 kD--.

Column 17, line 18, "M1 21 kD" should be --$M_l$ 21 kD--.

Column 19, line 42, "Wiconsin" should be --Wisconsin--.

UNITED STATES PATENT AND TRADEMARK OFFICE
CERTIFICATE OF CORRECTION

PATENT NO. : 5,276,269
DATED : January 4, 1994
INVENTOR(S) : Natasha V. Raikhel

It is certified that error appears in the above-indentified patent and that said Letters Patent is hereby corrected as shown below:

Column 19, line 63, "132:6-1" should be --132:6-13 --.

Column 20, line 10, the bracket "[" before "Plant" should be deleted.

Column 20, line 25, "mitrocellulose" should be --nitrocellulose--.

Column 20, line 43, "1 x 105" should be -- $1 \times 10^5$ --.

Column 20, line 58, before "-70°C", "t" should be replaced with --at--.

Column 21, line 1, "35 S" should be --$^{35}S$--.

Column 21, line 52, "Asn206" should be --$Asn_{206}$--.

Column 24, line 10- (Claim 2), "Claim 2" should read --Claim 1--.

UNITED STATES PATENT AND TRADEMARK OFFICE
CERTIFICATE OF CORRECTION

PATENT NO.  : 5,276,269
DATED       : January 4, 1994
INVENTOR(S) : Natasha V. Raikhel It is certified that error appears in the above-indentified patent and that said Letters Patent is hereby corrected as shown below:

```
Column 27, line 1 (Claim 3), "Claim 2" should read
--Claim 1--.
```

Signed and Sealed this

Fourth Day of October, 1994

BRUCE LEHMAN

*Attest:*

*Attesting Officer*     Commissioner of Patents and Trademarks